(12) United States Patent
Uchida et al.

(10) Patent No.: US 8,043,629 B2
(45) Date of Patent: Oct. 25, 2011

(54) BIOABSORBABLE SYNTHETIC NONWOVEN FABRIC HOLDING THROMBIN

(75) Inventors: Takanori Uchida, Kumamoto (JP); Noriko Shinya, Kikuchi (JP); Hiroshi Kaetsu, Kumamoto (JP); Takayuki Imamura, Kikuchi (JP); Chikateru Nozaki, Kikuchi (JP)

(73) Assignee: Juridical Foundation The Chemo-Sero-Therapeutic Research Institute, Kumamoto-Shi (JP)

( * ) Notice: Subject to any disclaimer, the term of this patent is extended or adjusted under 35 U.S.C. 154(b) by 523 days.

(21) Appl. No.: 11/941,779

(22) Filed: Nov. 16, 2007

(65) Prior Publication Data

US 2008/0286347 A1     Nov. 20, 2008

Related U.S. Application Data

(63) Continuation of application No. 10/534,715, filed as application No. PCT/JP03/014348 on Nov. 12, 2003, now abandoned.

(30) Foreign Application Priority Data

Nov. 14, 2002 (JP) .................................. 2002-330677

(51) Int. Cl.
*A61L 15/32* (2006.01)
*A61K 9/70* (2006.01)
*A61K 38/48* (2006.01)
*C12N 9/74* (2006.01)

(52) U.S. Cl. ..................... 424/445; 424/443; 424/94.64; 435/214; 442/123

(58) Field of Classification Search .................. 424/445, 424/443, 94.64; 435/214; 442/123
See application file for complete search history.

(56) References Cited

U.S. PATENT DOCUMENTS

| 4,265,233 A | 5/1981 | Sugitachi et al. |
| 5,843,096 A * | 12/1998 | Igaki et al. ..................... 606/151 |
| 6,056,970 A | 5/2000 | Greenawalt et al. |
| 2006/0051340 A1 | 3/2006 | Uchida et al. |

FOREIGN PATENT DOCUMENTS

| CA | 2504812 | | 5/1984 |
| CA | 2212832 | | 8/1996 |
| EP | 0 109 197 A | | 5/1984 |
| JP | 54-104687 | | 8/1979 |
| JP | 58-044057 | | 3/1983 |
| JP | 63095041 A | * | 4/1988 |
| WO | WO 90/13320 | | 11/1990 |
| WO | WO 99/59647 | | 11/1999 |

OTHER PUBLICATIONS

Neoveil. Product Information sheet from Gunze Co. downloaded from www.gunze.co.jp/medical/product/product_02.html on Sep. 16, 2010. p. 1-2.*
Supplementary European Search Report mailed Jan. 30, 2008.
Menyhart. 1995. Lyophilization: Freeze-drying. A downstream process. http://www.rpi.edu/dept/chem-eng/Biotech-Environ/LYO/, p. 1.
Office Action dated Mar. 3, 2011 issued by the Canadian Intellectual Property Office in corresponding Canadian Patent Application No. 2,504,812.

* cited by examiner

*Primary Examiner* — Taeyoon Kim
(74) *Attorney, Agent, or Firm* — Browdy and Neimark, PLLC

(57) ABSTRACT

A safe and effective hemostatic is provided. The invention relates to a bioabsorbable synthetic nonwoven fabric holding thrombin as an effective ingredient and a hemostatic comprising said bioabsorbable synthetic nonwoven fabric. The bioabsorbable synthetic nonwoven fabric holding thrombin in accordance with the present invention may be prepared by a process which comprises the steps of immersing a bioabsorbable synthetic nonwoven fabric into a solution containing thrombin and of lyophilizing the obtained nonwoven fabric. The bioabsorbable synthetic nonwoven fabric holding thrombin in accordance with the present invention allows for quicker and more effective hemostasis.

8 Claims, No Drawings

US 8,043,629 B2

BIOABSORBABLE SYNTHETIC NONWOVEN FABRIC HOLDING THROMBIN

This is a continuation of parent application Ser. No. 10/534,715 filed on May 12, 2005, now abandoned, which is the National Phase of PCT/JP03/014348 filed Nov. 12, 2003.

TECHNICAL FIELD

The present invention relates to a bioabsorbable synthetic nonwoven fabric characterized in that thrombin as an effective ingredient is held therein, a process for preparing the same and a hemostatic comprising said nonwoven fabric.

BACKGROUND ART

In the medical field, hemostatic management is very important. When the blood vessel in a living body is damaged, various coagulation factors are activated at that local area and fibrin is ultimately formed to thereby lead to hemostasis. In this process, thrombin is the most important enzyme that acts on fibrinogen so as to convert it into fibrin. Fibrinogen per se, though it is present in blood, has no hemostatic activity. It is upon the action of thrombin that the hemostatic activity is exerted. Namely, thrombin plays the most important role in a hemostatic reaction in a living body.

DISCLOSURE OF THE INVENTION

Technical Problem to be Solved by the Invention

Conventional thrombin preparations are in the form of liquid or powder and hence are often washed away when applied to the bleeding area, resulting in insufficient hemostatic effect of thrombin. For obviating this disadvantage, there have been various reports concerning sheets in which thrombin is held on bioabsorbable material (e.g. WO 90/13320 and Japanese Patent Publication No. 61/59737). One of these sheets is such that thrombin derived from blood is fixed on a sheet material made of gelatin. This sheet, however, as indicated in the Examples below, failed to show a sufficient hemostatic effect and is far from practical usage due to difficulty in its manufacture and problems when actually used. There is a hemostatic in the form of gel wherein bovine gelatin is mixed with bovine thrombin but this type of a hemostatic is also disadvantageous in that it has a risk for infection such as BSE and is not easy for compression procedure when used.

Another type of hemostatic is a fibrin adhesive in which thrombin is combined with other coagulation factors. A fibrin adhesive, mainly consisting of thrombin and fibrinogen, is a biological tissue adhesive that exploits conversion of fibrinogen to fibrin by the action of thrombin and has been widely used in the clinical field for the purpose of adhesion, hemostasis and sealing. However, for use in e.g. surgical operation, preparing a thrombin solution and a fibrinogen solution by dissolution takes time and hence it is very inconvenient for use especially in case of emergency.

In consideration of such inconvenience, a fibrin adhesive which is used by directly pressing to the bleeding area with a sheet is also in a practical usage. However, the currently available sheet type adhesive is not ideal since it consists of equine collagen as a basic material together with thrombin derived from bovine, i.e. material derived from non-human animal species, and hence there is a possibility that an antibody against heterologous proteins is elicited and a risk of zoonotic infections such as prion disease. Thus, the currently available topical hemostatics are not satisfactorily easy in handling and safe.

In order to solve the problems mentioned above, there is a need for a hemostatic comprising a coagulation factor that is derived from human and is free from an infectious agent, said hemostatic being in the form of a sheet made of a material that is strictly selected and devised for full achievement of a hemostatic effect and is safe to a living body.

Means for Solving the Problems

In view of the above-mentioned various problems, the present inventors have carried out intensive investigation and completed the present invention concerning a topical hemostatic. Thus, selecting a bioabsorbable synthetic material processed in the form of a nonwoven fabric among various bioabsorbable material, the present invention relates to a bioabsorbable synthetic nonwoven fabric holding thrombin as an effective ingredient for hemostasis, a process for preparation thereof, and a hemostatic comprising said nonwoven fabric.

More Efficacious Effects than Prior Art

The bioabsorbable synthetic nonwoven fabric holding thrombin in accordance with the present invention has excellent properties as listed below and hence is an ideal topical hemostatic.
(1) It has an excellent hemostatic effect;
(2) It can be handled with ease upon emergency;
(3) It is highly safe;
(4) It is absorbed with a lapse of time;
(5) It shows an excellent elasticity and flexibility;
(6) It enables for hemostasis at a broad area;
(7) It induces a slight or no inflammation reaction.

Accordingly, the present invention provides for a hemostatic comprising a bioabsorbable synthetic nonwoven fabric which allows for hemostasis with safe in such a surgical operation that requires for sealing of tissues in various fields of the operation.

BEST MODE FOR CARRYING OUT THE INVENTION

The bioabsorbable synthetic nonwoven fabric used in the present invention may be any nonwoven fabric made of a bioabsorbable synthetic fiber. The nonwoven fabric of the present invention has preferably appropriate flexibility to ensure that it may surely coat any affected area. For example, a synthetic fiber that may form such a nonwoven fabric includes polyglycolic acid, polylactic acid, or a copolymer of glycolic acid with lactic acid, etc., which may be used after processing into a nonwoven fabric. Among these, a bioabsorbable synthetic nonwoven fabric which is prepared from polyglycolic acid by processing into a nonwoven fabric is the most preferable material for the purpose of the present invention.

The nonwoven fabric of the present invention may be in any shape but preferably in the form of a sheet in view of versatility to various applications.

For thrombin, both thrombin derived from human blood and a recombinant thrombin obtained by the recombinant DNA technique may be used. In addition to thrombin, a pharmaceutically acceptable stabilizer and additive may also be added. Examples of such stabilizer and additive include, for instance, albumin, polyethylene glycol, arginine, sodium hyaluronate, glycerol, mannitol and calcium chloride etc.

The bioabsorbable synthetic nonwoven fabric holding thrombin in accordance with the present invention may be manufactured, for instance, as described below.

Thrombin is dissolved in a saline or a buffer and thereto is further added optionally albumin, polyethylene glycol, arginine, hyaluronic acid, glycerol, mannitol, or calcium chloride etc. as a stabilizer or an additive. A bioabsorbable synthetic nonwoven fabric is then immersed into the solution, frozen at −80° C. for 2 hours and lyophilized to give a desired product.

The bioabsorbable nonwoven fabric holding thrombin according to the present invention may be pressed onto a bleeding area to prevent outflow of blood through pressure and besides thrombin contained in the sheet instantly reacts with fibrinogen in the blood to render fibrinogen be converted to fibrin to thereby achieve a hemostatic effect at the local area. The formed fibrin may adhere to the surrounding tissues.

A bioabsorbable nonwoven fabric made of polyglycolic acid has already been used for a medical purpose and its safety has been proved as being absorbed into the living body and being decomposed into water and carbon dioxide.

INDUSTRIAL APPLICABILITY

As such, the bioabsorbable nonwoven fabric holding thrombin according to the present invention may easily and quickly be applied to topical bleeding and allows for efficient hemostasis through both pressure and a blood coagulation reaction. Besides, since every material used in said bioabsorbable nonwoven fabric is safe to the living body, it may be used in a clinical situation without care.

The present invention is explained in more detail by means of the following Examples but should not be construed to be limited thereto.

Example 1

Preparation of Recombinant Thrombin

A recombinant thrombin was prepared as described in Japanese Patent Application No. 2001/206,919. Briefly, animal cells to which a human prethrombin gene is introduced are cultured and prethrombin is then purified from the resulting culture medium. On the other hand, ecarin is purified from a culture medium of animal cells into which ecarin gene is introduced. Prethrombin is activated by ecarin as obtained to thereby provide thrombin that may be purified.

Example 2

Preparation of Sheet Holding Thrombin

A sheet holding thrombin in accordance with the present invention was prepared by the process as described below.

To a solution containing 0.001 to 0.01% sodium hyaluronate (nacalai tesque; 18237-41) or 0.5 to 2% glycerol (nacalai tesque; 17018) are added mannitol (nacalai tesque; 21303) at a final concentration of 0.5 to 1.5% and 40 mM calcium chloride and subsequently the recombinant thrombin at a final concentration of 1000 U/mL. The solution is added dropwise to a bioabsorbable synthetic nonwoven fabric made of polyglycolic acid (3 cm×3 cm; Neoveil, Gunze Limited, thickness 0.15 mm) at 0.05 mL/cm$^2$. The sheet, after being frozen at −80° C. for 2 hours and lyophilized, is used as a sample of a sheet holding recombinant thrombin. Similarly, a sheet holding thrombin derived from blood is prepared using thrombin derived from human blood instead of the recombinant thrombin.

As a control, a bioabsorbable synthetic nonwoven fabric not treated with thrombin, a hemostatic sponge made of gelatin prepared as described in Examples of WO 90/13320 and a commercially available fibrin adhesive in sheet were used.

Group 1: Sheet Holding Thrombin Derived from Blood

A sheet was used where thrombin derived from human blood was held in a nonwoven fabric made of polyglycolic acid at 50 U/cm$^2$.

Group 2: Sheet Holding Recombinant Thrombin

A sheet was used where a recombinant thrombin was held in a nonwoven fabric made of polyglycolic acid at 50 U/cm$^2$.

Group 3: Sheet with No Thrombin

A sheet was used where a nonwoven fabric made of polyglycolic acid was treated as in Group 1 with no thrombin.

Group 4: Hemostatic Sponge with Fixed Thrombin

A hemostatic sponge made of gelatin containing thrombin derived from human blood was used that was prepared as described in Examples of WO 90/13320 (Spongostan, Johnson & Johnson K.K.).

Group 5: Fibrin Adhesive in Sheet

A fibrin adhesive in sheet where components of a fibrin adhesive are fixed on a collagen sheet (TachoComb, Torii Pharmaceutical Co., Ltd.) was used wherein components such as fibrinogen and thrombin were fixed by lyophilization on one side of a sponge sheet made of equine collagen.

Example 3

Test for Hemostasis in Exudative Bleeding

Rabbit was used as an animal model for assessing hemostasis. Rabbit was subject to abdominal section and a part of the liver was excised, to which bleeding area each hemostatic of the groups as prepared in Example 2 was applied for a whole area of the wound and was pressed for a minute. Assessment used was as indicated below.

(1) Rabbit was subject to abdominal section under anesthesia with Nembutal.

(2) Heparin was intravenously administered at 300 U/kg.

(3) The surface of the right lobe, the inner left lobe or the outer left lobe of the liver was excised in a shape of circle of 1.5 cm diameter with thickness of 4 mm.

(4) Bleeding from the excised wound was absorbed with gauze for 10 seconds and weighed. An amount of bleeding after generation of the excised wound was about 0.50 g.

(5) Attempt to cease bleeding was done with various hemostatic means as mentioned above. Each treatment was conducted without a vascularization but with blood flowing out.

(6) Bleeding for 5 minutes, including the time required for the hemostatic treatment, was absorbed with gauze and weighed. When bleeding from the wound surface was observed after 5 minutes, the hemostatic treatment and the weighing of bleeding were repeated.

(7) The hemostatic treatment was repeated for at most four times and assessment was made with a frequency of the hemostatic treatment needed for hemostasis and a total weight of bleeding from the initiation of the hemostatic treatment up till hemostasis (Table 1).

TABLE 1

| Group | 1st | 2nd | 3rd | 4th | Total bleeding after hemostatic treatments/g |
|---|---|---|---|---|---|
| 1 | 7 | 1 | 0 | 0 | 0.51 ± 0.31 |
| 2 | 7 | 1 | 0 | 0 | 0.34 ± 0.15 |
| 3 | 2 | 3 | 3 | 0 | 2.03 ± 0.95 |
| 4 | 0 | 2 | 4 | 2* | 6.28 ± 1.67 |
| 5 | 0 | 4 | 1 | 3* | 6.70 ± 2.64 |

Header note: "No. of cases in which hemostasis was achieved with each of hemostatic treatment" spans columns 1st–4th.

*Even after the fourth hemostatic treatment, cases were observed where hemostasis was not possible.

As shown in Table 1, the sheet holding thrombin of the present invention was found to exhibit a more excellent hemostatic effect in both thrombin derived from blood (Group 1) and a recombinant thrombin (Group 2) than that of the control sheets. With a nonwoven fabric alone with no thrombin treatment (Group 3), a hemostatic effect was scarcely observed but was even higher than that of the hemostatic sponge made of gelatin with fixed thrombin (Group 4) as described in WO 90/13320. This indicates that, among the known bioabsorbable material, a bioabsorbable nonwoven fabric used in the present invention as a substrate is the most suitable material for use in hemostasis. It was further revealed that holding thrombin in this nonwoven fabric allowed for quicker and more effective hemostasis. Besides, as is clear from the results of the comparative test, the fibrin adhesive in sheet where collagen is used as a substrate (Group 5) showed far less hemostatic effect as compared to the sheet holding thrombin of the present invention.

What is claimed is:

1. A bioabsorbable synthetic non-woven fabric holding a hemostatic-effective amount of thrombin,
    said non-woven fabric being made of a material comprising polyglycolic acid,
    said non-woven fabric having sufficient elasticity and flexibility for sealing tissues of various shapes,
    formed by contacting a bioabsorbable synthetic non-woven fabric with a saline solution comprising thrombin optionally containing a pharmaceutically acceptable additive selected from the group consisting of albumin, polyethylene glycol, arginine, hyaluronic acid, glycerol, mannitol and calcium chloride, and lyophilizing the non-woven fabric holding the thrombin,
    said bioabsorbable synthetic non-woven fabric being formed by said contacting of the bioabsorbable synthetic nonwoven fabric with the saline solution, wherein said saline solution consists of said thrombin alone or said thrombin containing said pharmaceutically acceptable additive.

2. The bioabsorbable synthetic nonwoven fabric of claim 1 which is free of fibrinogen.

3. The bioabsorbable synthetic nonwoven fabric according to claim 1, wherein the thrombin is thrombin derived from human blood or a recombinant human thrombin produced by a recombinant DNA technique.

4. The bioabsorbable synthetic nonwoven fabric of claim 1, formed by freezing prior to said lyophilizing.

5. The bioabsorbable synthetic nonwoven fabric formed by contacting a bioabsorbable synthetic nonwoven fabric with a saline solution of thrombin of claim 1, wherein the pharmaceutically acceptable additive is present in the saline solution.

6. The bioabsorbable synthetic nonwoven fabric formed by contacting a bioabsorbable synthetic nonwoven fabric with a saline solution of thrombin of claim 4, wherein the pharmaceutically acceptable additive is present in the saline solution.

7. The bioabsorbable synthetic nonwoven fabric according to claim 1 in sheet form.

8. The bioabsorbable synthetic nonwoven fabric according to claim 6 in sheet form.

* * * * *